(12) United States Patent
Lautamo

(10) Patent No.: US 7,390,349 B2
(45) Date of Patent: Jun. 24, 2008

(54) POLYHYDROSILOXANE COMPOUNDS AND ARTICLES AND USE THEREOF

(75) Inventor: Roy M A Lautamo, Placerville, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 488 days.

(21) Appl. No.: 10/913,611

(22) Filed: Aug. 5, 2004

(65) Prior Publication Data

US 2006/0027098 A1 Feb. 9, 2006

(51) Int. Cl.
*B01D 53/02* (2006.01)

(52) U.S. Cl. .......................................................... 95/88
(58) Field of Classification Search ...................... 95/82, 95/88

See application file for complete search history.

(56) References Cited

U.S. PATENT DOCUMENTS

2004/0129141 A1 * 7/2004 Malik et al. .................... 96/101

FOREIGN PATENT DOCUMENTS

| FR | 2647456 | | 11/1990 |
| JP | 03012425 A | * | 1/1991 |
| JP | 403012425 | | 1/1991 |
| WO | WO 02/072225 A1 | | 9/2002 |

OTHER PUBLICATIONS

EPO Search Report, Nov. 10, 2005, 2 pages.

Markides, et al., "Deactivation of Fused Silica Capillary Columns with Phenylhydrosiloxanes," Journal of High Resolution Chromatography & Chromatography Communications, vol. 8, Aug. 1985, pp. 378-384, 7 pgs.
Woolley, et al., "Deactivation of Small Diameter Fused Silica Capillary Columns with Organosilicon Hydrides," Journal of High Resolution Chromatography & Chromatography Communications, vol. 9, Sep. 1986, pp. 506-514, 9 pgs.
Itoh, et al., "Side-chain liquid-crystalline polymers with silphenylene-siloxane main chains," Journal of Polymer Science, Part A: Polymer Chemistry (1991), pp. 1399-1406 (1 page Abstract).
T. Welsch, et al., "High Resolution Chromatography and Chromatography Communications," 11 (1988) 471.
T. Welsch, et al., "Chromatographia," 10 (1977) 22.
L. Blomberg, et al., "Proceedings of the Fourth International Symposium on Capillary Chromatography," Huethig, Heidelberg (1981) pp. 73-89.
C.L. Woolley, et al., "High Resolution Chromatography & Chromatography Communications," 7 (1984) 329.
K.E. Markides, et al., "High Resolution Chromatography & Chromatography Communications," 8 (1985) 741.

* cited by examiner

*Primary Examiner*—Robert A Hopkins

(57) ABSTRACT

The present disclosure, in embodiments, provides a compound of the formula

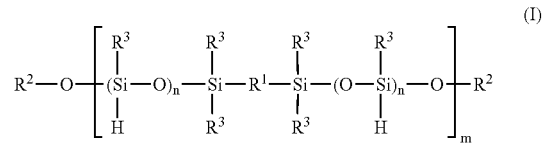

(I)

where $R^1$, $R^2$, $R^3$, n, and m are as defined in the specification. The disclosure also provides an article including: a fused silica capillary column treated with a compound of the formula (I), and optionally coated with a stationary phase. The disclosure also provides a separation method, including chromatographing a mixture of compounds on the article.

15 Claims, 3 Drawing Sheets

INCREASING TIME (minutes) →

INCREASING TIME (minutes) →

INCREASING TIME (minutes) →

INCREASING TIME (minutes) →

POLYHYDROSILOXANE COMPOUNDS AND ARTICLES AND USE THEREOF

BACKGROUND

Gas chromatography equipment is known and can be used, for example, in chemical analysis or diagnostics, to separate and identify chemical compounds in mixtures or in isolation. Certain chemical compounds are known which can be used, for example, to deactivate fused silica capillary columns or like articles used in gas chromatography equipment.

SUMMARY

In general terms, the claimed invention relates to certain polyhydrosiloxane compounds and their use to deactivate fused silica capillary columns or like articles, used in chromatography, for example, gas chromatography equipment.

One possible aspect of the disclosure is a compound of the formula (I)

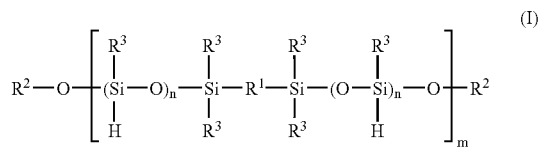

wherein
$R^1$ is a divalent spacer group selected from —Ar—,
$(C_1$-$C_4)$alkyl substituted —Ar—,
—$(CH_2)_k$—Ar—$(CH_2)_k$—,
$(C_1$-$C_4)$alkyl substituted —$(CH_2)_k$—Ar—$(CH_2)_k$—,
—Ar—Ar—,
$(C_1$-$C_4)$alkyl substituted —Ar—Ar—,
—$(CH_2)_k$—Ar—Ar—$(CH_2)_k$—,
$(C_1$-$C_4)$alkyl substituted —$(CH_2)_k$—Ar—Ar—$(CH_2)_k$—,
—$(CH_2)_k$—Ar—$(CH_2)_k$—Ar—$(CH_2)_k$—,
$(C_1$-$C_4)$alkyl substituted —$(CH_2)_k$—Ar—$(CH_2)_k$—Ar—$(CH_2)_k$—,
—Ar—O—Ar—, $(C_1$-$C_4)$alkyl substituted —Ar—O—Ar—,
—$(CH_2)_k$—Ar—O—Ar—$(CH_2)_k$—,
$(C_1$-$C_4)$alkyl substituted —$(CH_2)_k$—Ar—O—Ar—$(CH_2)_k$—,
saturated or unsaturated —$(C_1$-$C_6)$alkylene-,
$(C_1$-$C_4)$alkyl substituted saturated or unsaturated —$(C_1$-$C_6)$alkylene-;
Het, $(C_1$-$C_4)$alkyl substituted -Het-,
—$(CH_2)_k$-Het-$(CH_2)_k$—,
$(C_1$-$C_4)$alkyl substituted —$(CH_2)_k$-Het-$(CH_2)_k$—,
—Ar—$(CH_2)_k$—,
$(C_1$-$C_4)$alkyl substituted —Ar—$(CH_2)_k$—,
Ar'—CH=, or
$(C_1$-$C_4)$alkyl substituted Ar'—CH=;
$R^2$ is an end cap group;
$R^3$ are each independently a branched or unbranched $(C_1$-$C_4)$alkyl or -Ph;
k is an integer from 1 to about 10;
n is an integer from 1 to about 10; and
m is an integer from 1 to about 10.

Another possible aspect of the disclosure is an article comprising a fused silica capillary column treated with a compound of the formula (I) and optionally coated with a layer forming a stationary phase.

Another possible aspect of the disclosure is a separation method, comprising separating or chromatographing a mixture of compounds on a fused silica capillary column deactivated with a compound the formula (I) and optionally coated with a layer which forms a stationary phase.

Another possible aspect of the disclosure is a method of deactivating a fused silica capillary column comprising treating the column with a compound of the formula (I).

DETAILED DESCRIPTION

Figure 1:
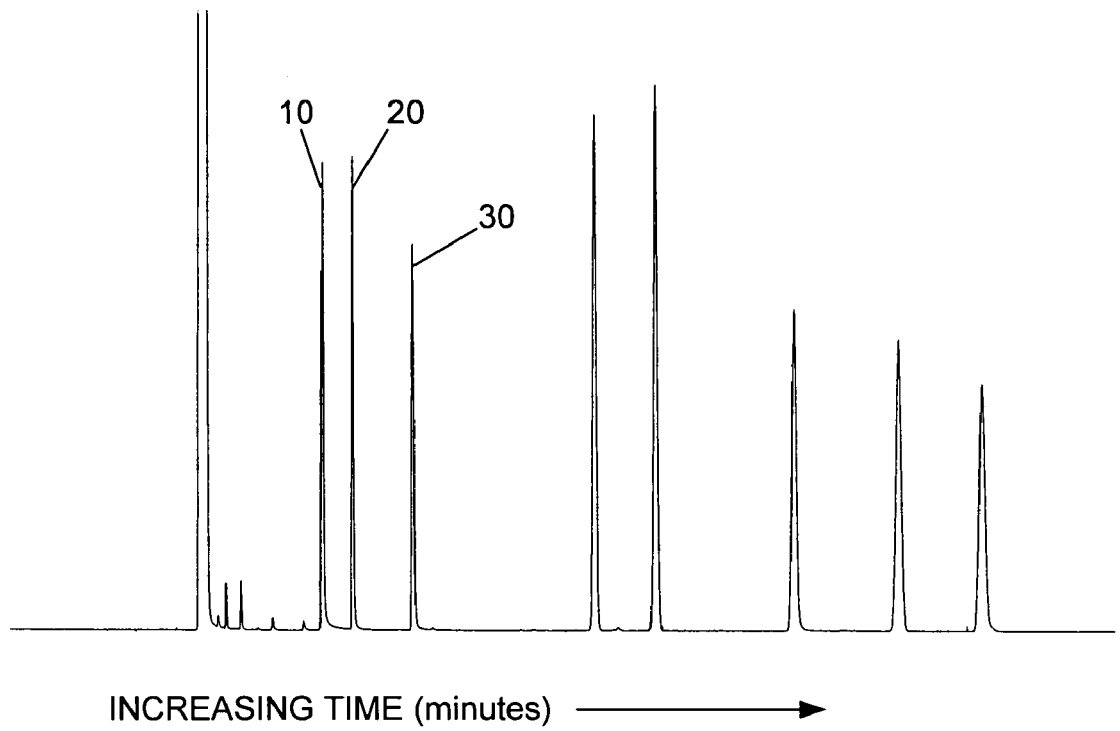
FIG. 1 illustrates a comparative chromatogram of a first mixture of analyte compounds separated on a capillary column deactivated with a known disilazane compound.

Various embodiments of the present disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

The present disclosure provides, in embodiments, a compound of the formula (I)

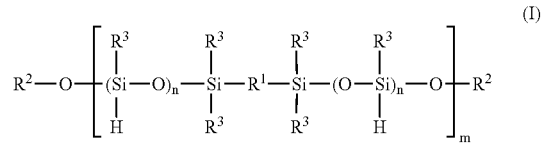

where $R^1$, $R^2$, $R^3$, n, and m are as defined herein. The disclosure also provides an article including: a fused silica capillary column treated with a compound of the formula (I), and optionally coated with layer forming a stationary phase. "Fused silica" and like terms refer to silica ($SiO_2$) which has been, for example, heated at high temperature and pressure to provide a product comprised predominantly of a bulk network of repeating (Si—O—) bonds and having surface silanol groups (Si—OH) which are reactive. For additional definitions, descriptions, and methods of silica materials, see for example, R. K. Iler, The Chemistry of Silica, Wiley-Interscience, 1979, the entirety of which is incorporated by reference herein. "Capillary column" includes any tube-like passage which can have on its inner surface reactive silanol groups (Si—OH) or like reactive groups, such as Si—X where X is a substitutable, displaceable (leaving group), or blockable group, such as —OH, and like groups. One possible example of a capillary column can include a small diameter tubing, such as fused silica glass, nanotubes, microtubes, vias on or within silicon wafers, having reactive silanol groups (Si—OH), or like reactive groups on an enclosed surface which can be passivated or deactivated with the compounds and methods of the disclosure. "Passivate" or "deactivate" or like terms refer to surface treatment processes of the present disclosure, which make the treated surface inactive, less reactive, or selectively interactive with respect to the analyte compounds. Another possible example of a capillary column, or like suitable article, can include, for example, stainless steel tubing that has been treated with silane gas to form a silicon layer on the inside surface. The resulting silicon layer readily oxidizes to from a surface layer of silica ($SiO_2$) having reactive silanol groups (Si—OH). In the present disclosure for convenience textual representation of silicon compounds or portions thereof, such as silanol groups (Si—OH) do not show the four valances of typical tetravalent silicon atoms and compounds. "Stationary phase" and like terms refer to the material to be coated on the deactivated surface produced by reaction or association of the polyhydrosiloxane compound, polyhydrosiloxane oligomers, polyhydrosiloxane copolymers, or mixtures thereof, of the disclosure with a fused silica capillary or like reactive surface. In general, a stationary phase refers to a material over which a mobile phase flows. As a sample solution flows with the mobile phase through the stationary phase, the components of that solution will migrate according to the non-covalent interactions of the compounds with the stationary phase. The interactions of the sample with the stationary phase and the mobile phase, determines the degree of migration and separation of the components contained in the sample. For example, those samples which have stronger interactions with the stationary phase than with the mobile phase will elute from the column less quickly, and thus have a longer retention time, while samples which have weaker interactions with the stationary phase than with the mobile phase will elute from a column more quickly.

Although not desired to be limited by theory, in gas chromatography the mobile phase does not interact with the sample. The mobile phase carrier gas only carries the sample molecules down the capillary when they are in vapor phase. There is no effect on relative elution due to carrier gas type. Only temperature affects elution due to changes in vapor pressure.

In embodiments, the present disclosure overcomes problems of differential or non-homogenous separation of the same analyte on a chromatography column, for example, where the same molecules can encounter dissimilar interactions or dissimilar environments among the column's surfaces, such as the stationary phase or the column surface itself. Differential or non-homogenous separation can lead to undesirable phenomena such as "tailing" and decreased resolution or separation of similar but non-identical analyte compounds. In embodiments, the present disclosure provides separation articles and separation methods which provide homogenous separation of the same analyte having, for example, reduced or eliminated tailing and increased resolution of individual components and among similar components.

In various embodiments, halo includes fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

"Alkyl" includes linear alkyls, branched alkyls, and cycloalkyls.

"Substituted alkyl" or "optionally substituted alkyl" refers to an alkyl substituent, which includes linear alkyls, branched alkyls, and cycloalkyls, having from 1 to 4 optional substituents selected from hydroxyl (—OH), halogen, amino (—$NH_2$), nitro (—$NO_2$), alkyl, acyl (—C(=O)R), alkylsulfonyl (—S(=O)$_2$R) or alkoxy (—OR). For example, an alkoxy substituted alkyl, can be a 2-methoxy substituted ethyl of the formula —$CH_2$—$CH_2$—O—$CH_3$, a 1-dialkylamino substituted ethyl of the formula —$CH_2$($NR_2$)—$CH_3$, and like substituted alkyl substituents.

"Aryl" includes a phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents.

"Het" includes a four-(4), five-(5), six-(6), or seven-(7) membered saturated or unsaturated heterocyclic ring having 1, 2, 3, or 4 heteroatoms selected from the group consisting of oxy, thio, sulfinyl, sulfonyl, and nitrogen, which ring is optionally fused to a benzene ring. Het also includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, ($C_{1-4}$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, ($C_1$-$C_7$)alkyl or $C_{1-7}$alkyl refers to alkyl of one to seven carbon atoms, inclusive, and ($C_1$-$C_4$)alkyl or $C_{1-4}$alkyl refers to alkyl of one to four carbon atoms, inclusive.

The compounds of the present disclosure are generally named according to the IUPAC nomenclature system. Abbreviations, which are well known to one of ordinary skill in the art, may be used (e.g., "Ph" for phenyl, "Me" for methyl, "Et" for ethyl, "h" for hour or hours, "g" or "gm" for gram(s), "mL" for milliliters, and "rt" for room temperature).

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

"Consisting essentially of" in embodiments refers, for example, to a single compound, mixture of compounds, or a composition, the method of using the compound or compounds to deactivate capillary columns, and the resulting deactivated capillary column articles of the disclosure, and can include the components or steps listed in the claim, plus other components or steps that do not materially affect the basic and novel properties of the compounds, articles, and methods of use of the disclosure, such as the particular substrates, particular column pretreatments, or like structure or process variables selected. Items that may materially affect the basic properties of the components or steps of disclosure may impart undesirable characteristics to the present disclosure include, for example, decreased separation, decreased resolution, increased tailing, and like characteristics. In embodiments, the compounds, the articles, or the methods of the present disclosure preferably eliminate or avoid such undesirable characteristics.

The indefinite article "a" or "an" and its corresponding definite article "the" as used herein means at least one, or one or more, unless specified otherwise.

Specific and preferred values listed below for radicals, substituents, and ranges, are for illustration only; they do not exclude other defined values or other values within defined ranges for the radicals and substituents. The compounds of the disclosure include compounds of formulas (I and II) and like compounds having any combination of the values, specific values, more specific values, and preferred values described herein.

Specifically, aryl can be phenyl, naphthyl, anthracenyl, phenanthrenyl, fluorenyl, tetrahydronaphthyl, or indanyl.

Specifically, $C_{1-4}$alkyl can be methyl, ethyl, propyl, isopropyl, butyl, iso-butyl, sec-butyl, tert-butyl; $C_{1-7}$alkyl can be methyl, ethyl, propyl, isopropyl, butyl, iso-butyl, sec-butyl, tert-butyl, pentyl, 3-pentyl, hexyl, or heptyl; $(C_{3-12})$cycloalkyl can be cyclopropyl, cyclobutyl, cyclopentyl, cyclohexyl, cycloheptyl, cyclooctyl, bicyclic, or multi-cyclic substituents, such as of the formulas

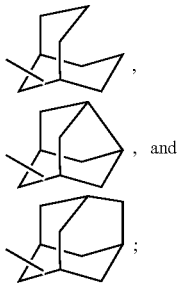

$C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; —C(=O)alkyl or ($C_{2-7}$)alkanoyl can be acetyl, propanoyl, butanoyl, pentanoyl, 4-methylpentanoyl, hexanoyl, or heptanoyl; aryl can be phenyl, indenyl, or naphthyl; Het can be pyrrolidinyl, piperidinyl, morpholinyl, thiomorpholinyl, or heteroaryl; and heteroaryl can be furyl, imidazolyl, triazolyl, triazinyl, oxazolyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specifically, —$(CH_2)_k$— can be a —$(C_{1-10}$alkylene)- when k is an integer from 1 to about 10, which can be methylenyl, ethylenyl, propylenyl, butylenyl, pentylenyl, 3-pentylenyl, hexylenyl, heptylenyl, octylenyl, nonylenyl, or decylenyl.

Specifically, —$(CH_2)_k$— can be a —$(C_{1-7}$alkylene)- when k is an integer from 1 to about 7, or from 1 to about 5, which can be methylenyl, ethylenyl, propylenyl, butylenyl, pentylenyl, 3- or pentylenyl.

Specifically, —$(CH_2)_k$— can be a —$(C_{1-4}$alkylene)- when k is an integer from 1 to about 4, which can be methylenyl, ethylenyl, propylenyl, or butylenyl.

A specific value for Het includes a five-(5), six-(6), or seven-(7) membered saturated or unsaturated ring containing 1, 2, 3, or 4 heteroatoms, for example, non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic Het diradical thereto.

A specific compound is of the formula (I) wherein $R^1$ is —$(CH_2)_k$—Ar—$(CH_2)_k$—, or $(C_1\text{-}C_4)$alkyl substituted —$(CH_2)_k$—Ar—$(CH_2)_k$—, where Ar can be, for example, an ortho-, meta-, or para-substituted —$C_6H_4$—, k can be, for example, an integer from 1 to about 5; $R^2$ can be, for example, —$Si(CH_3)_3$; $R^3$ can be, for example, —$CH_3$; n can be, for example, an integer from 1 to about 5; and m is an integer from 1 to about 5.

A specific compound is of the formula (I) wherein $R^1$ can be, for example, —$CH_2$—Ar—$CH_2$—, or $(C_1\text{-}C_4)$alkyl substituted —$CH_2$—Ar—$CH_2$—, where Ar can be, for example, an ortho-, meta-, or para-substituted —$C_6H_4$—; —Ar—$CH_2$—, or $(C_1\text{-}C_4)$alkyl substituted —Ar—$CH_2$— where Ar can be, for example, an ortho-, meta-, or para-substituted —$C_6H_4$—, such as —$C_6H_4$—$CH_2$—, or optionally alkyl substituted —$C_6H_4$—$CH_2$—, for example, $(C_1\text{-}C_4)$alkyl substituted or like substituted $R^1$ groups of the core formula —$C_6H_4$—$CH_2$—, such as —$C_6H_3(R)$—$CH_2$— or —$C_6H_4$—CH(R)— where R can be $(C_1\text{-}C_4)$alkyl or substituted $(C_1\text{-}C_4)$alkyl; and Ar'—CH=, or $(C_1\text{-}C_4)$alkyl substituted Ar'—CH=, where each Ar' has a substituent connected to the main chain, that is for example, where each Ar' can have, for example, a single substituent for backbone or polymer chain connectivity; $R^2$ can be, for example, —$Si(CH_3)_3$; $R^3$ can be, for example, —$CH_3$; n is an integer from 1 to about 5; and m can be, for example, an integer from 1 to about 5.

"$(C_1\text{-}C_4)$alkyl substituted" refers to having a $(C_1\text{-}C_4)$alkyl substituent attached to the aromatic or heteroaromatic portion of the hydrocarbon moiety, having a $(C_1\text{-}C_4)$alkyl substituent attached to the substituents attached to the aromatic or heteroaromatic portion of the hydrocarbon moiety, or both. Thus, a $(C_1\text{-}C_4)$alkyl substituted —$CH_2$—$C_6H_4$—$CH_2$—, can be, for example, —$CH_2$—$C_6H_4$—$CH_2$— having one or more $(C_1\text{-}C_4)$alkyl substituent attached to the —$C_6H_4$—, one or more $(C_1\text{-}C_4)$alkyl substituent attached to either or both of the —$CH_2$— substituents, or both, such as —$CH_2$-(3-Et-$C_6H_3$)—$CH_2$—, —CH(Et)-$C_6H_4$—CH(Et)-, —CH(Et)-(3-Et-$C_6H_3$)—CH(Et)-, and like patterns.

"1,4-Substituted," "para-substituted," or like prefixes refer to the substitution pattern of intra-chain or backbone substituents on an aromatic or heteroaromatic portion of the hydrocarbon core. Thus, for example, "1,4-substituted —$CH_2$—$C_6H_4$—$CH_2$—$CH_2$—" or simply 1,4-(—$CH_2$—$CH_2$-$C_6H_4$—$CH_2$—$CH_2$—) refer to para-substituted version of a diethylenyl phenyl hydrocarbon moiety.

Polymer chain connectivity of the hydrocarbon moieties can be achieved either as a pendant group attached to the chain, or preferably intra-chain (within or as an integral part of the backbone or chain). Intra-chain connectivity, for example, in a six membered aromatic hydrocarbon ring such as —($C_6H_4$)—, can be ortho- or 1,2-, meta- or 1,3-, and para- or 1,4-substitution patterns while heteroaromatic ring such as piperidinyl —($C_5H_3N$)—, can be 2,3-, 2,4-, 2,5-, and 2,6-substitution patterns. A preferred hydrocarbon is a dialkylene substituted aromatic hydrocarbons of the formula —$(CH_2)_k$—Ar—$(CH_2)_k$— or $(C_1$-$C_4)$alkyl substituted —$(CH_2)_k$—Ar—$(CH_2)_k$—, where k is an integer from 1 to 10, such as 1,2-, 1,3- or 1,4-dimethylene or -diethylene substituted —Ar— of the formula —$CH_2$—Ar—$CH_2$— or —$CH_2$—$CH_2$—Ar—$CH_2$—$CH_2$—, and more preferably 1,4-dimethylene or -diethylene substituted —$C_6H_4$— of the formula —$CH_2$—$C_6H_4$—$CH_2$— or —$CH_2$—$CH_2$—$C_6H_4$—$CH_2$—$CH_2$—. For pendant hydrocarbon moieties, such as aromatic hydrocarbons of the formula —Ar—$(CH_2)_k$—, or $(C_1$-$C_4)$alkyl substituted —Ar—$(CH_2)_k$—, each pendant hydrocarbon moiety has one aromatic atom and at least a one substituent, which is other than atoms of the aromatic hydrocarbon, that provide for hydrocarbon polymer chain connectivity. "Hydrocarbon" and like terms, in the context of the polyhydrosiloxane compounds of the present disclosure, refer to divalent —$R^1$— moieties, and can include, but is not limited to, for example, alkyl hydrocarbons, aromatic or aryl hydrocarbons, alkyl substituted aryl hydrocarbons, alkoxy substituted aryl hydrocarbons, heteroalkyl hydrocarbons, heteroaromatic or heteroaryl hydrocarbons, alky substituted heteroaryl hydrocarbons, alkoxy substituted heteroaryl hydrocarbons, and like hydrocarbon moieties, and as illustrated herein. In embodiments, the hydrocarbon of the polyhydrosiloxane compound is selected to be the same, similar to, or at least chemically or physically compatible with those hydrocarbons contained in the stationary phase.

Another specific compound is of the formula (I) wherein $R^1$ is a para-substituted or a 1,4-dialkylene substituted phenyl, such as of the formula —$CH_2$—$C_6H_4$—$CH_2$—; $R^2$ is —Si$(CH_3)_3$; $R^3$ are each —$CH_3$; n is 4; and m is an integer from 1 to about 3.

Another specific compound of formula (I) is a compound of the formula (II)

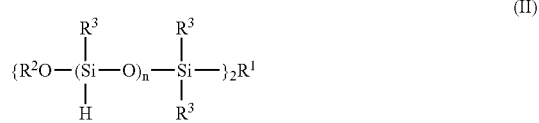

(II)

wherein $R^1$ is a 1,4-substituted —$CH_2$—$C_6H_4$—$CH_2$—; $R^2$ is —Si$(CH_3)_3$; $R^3$ is —$CH_3$; and n is an integer from 1 to about 4.

Another specific compound of formula (I) is a compound of the formula (I) wherein $R^1$ is obtained from alpha, alpha'-bis(dimethylmethoxysilyl)p-xylene of the formula

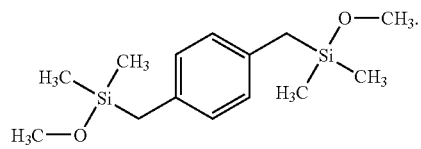

Another specific compound of formula (I) is a compound of the formula (I) wherein $R^1$ is obtained from beta,beta'-bis(dimethylethoxysilyl)1,4-diethylbenzene of the formula

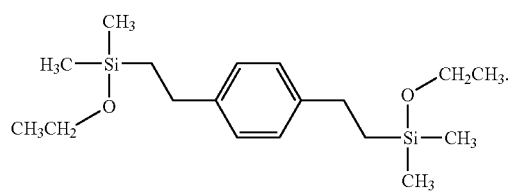

Another specific compound of formula (I) is a compound of the formula (I) wherein $R^1$ is obtained from the bis(dimethylethoxysilyl) substituted toluene compound (1-(Ethoxy-dimethyl-silanyl)-4-[(ethoxy-dimethyl-silanyl)-methyl]-benzene) of the formula

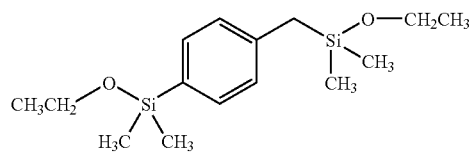

The abovementioned specific compounds of the formula (I), and like compounds of the disclosure, can include a salt or salts thereof.

Polyhydrosiloxane compounds of the disclosure, such as the abovementioned compounds of formula (I), can be prepared as described and illustrated herein, for example in the scheme below, by procedures analogous thereto, or by many different procedures, including the procedures in the above mentioned publications or patents. All of the variables used in the scheme(s) are as defined below or elsewhere herein. Scheme 1 first illustrates the preparation of a compound of the disclosure, such as by the reaction of one or more equivalents of tetramethylcyclotetrasiloxane (TMCTS) or like reactants, and one or more equivalents of a divalent hydrocarbon spacer unit, such as alpha,alpha'-bis(dimethylmethoxysilyl)p-xylene, for example, in the presence of a solvent, and a suitable catalyst. An end cap reagent or protecting group, such as trimethylsilyl chloride ($Me_3SiCl$), tri-tert-butylsilyl chloride (t-$Bu_3SiCl$), trimethylmethoxysilane ($Me_3Si(OMe)$), or like reagents can be added in various amounts depending upon molecular weight properties desired, for example, during or after the reaction of the siloxane and hydrocarbon reactants. In embodiments, trimethylmethoxysilane ($Me_3Si(OMe)$) is a preferred protecting group reagent, for example, because the methanol by-product is less troublesome. Second, Scheme 1 illustrates the reaction of the resulting polyhydrosiloxane compound, or like oligomers, copolymers, or mixtures thereof, with a fused silica surface to provide a silica surface having the siloxane bound thereto. The reaction between each silylhydride (Si—H) group of the polyhydrosiloxane with a Si—OH group on the fused silica surface to form a Si—O—Si may be complete (i.e., no Si—H groups remaining unreacted) or incomplete depending, for example, on the conditions selected, such as the heating temperature, the duration of heating, the flexibility of the polyhydrosiloxane compound or copolymer, the availability or accessibility of the surface Si—OH groups, the availability of excess polyhydrosiloxane relative to surface Si—OH groups, and like considerations.

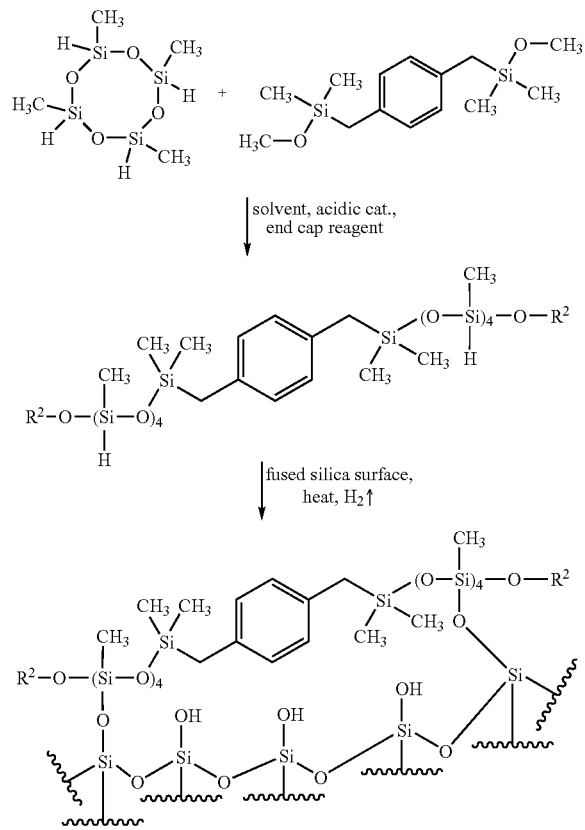

The non-covalently bonded divalent hydrocarbon spacer unit can generally provide the resulting silica bound siloxane surface with distinctive sites, pores, cavities, or the like surface structures, having both pi-type hydrophobic character (attributable to the aromatic or heteroaromatic portion of the spacer) and silanol-type hydrophilic character (attributable to the proximal unreacted silica surface silanol groups). The dimensions, chemical character, and chromatographic performance of the resulting deactivated surfaces and their surface structures can be a priori engineered or readily altered post hoc by, for example, molecular modeling of geometries, surface energies, and like functional properties of possible or desired surface structures and the target analytes, appropriate selection of the deactivation compound starting materials and their stoichiometries, and evaluation of the performance characteristics, such as chromatographic separation results obtained from column articles incorporating the deactivated surfaces of the disclosure.

Other conditions suitable for formation and modification of the compounds, oligomers, copolymers, or like products of the disclosure, from a variety of starting materials or intermediates, as illustrated herein are known. For example, see Feiser and Feiser, "Reagents for Organic Synthesis", Vol. 1, et seq., 1967; March, J. "Advanced Organic Chemistry," John Wiley & Sons, 4$^{th}$ ed. 1992; House, H. O., "Modem Synthetic Reactions," 2$^{nd}$ ed., W. A. Benjamin, New York, 1972; and Larock, R. C., "Comprehensive Organic Transformations," 2$^{nd}$ ed., 1999, Wiley-VCH Publishers, New York, the entireties of which are incorporated by reference herein.

The starting materials employed in the synthetic methods described herein are commercially available, have been reported in the scientific literature, or can be prepared from readily available starting materials using procedures known in the field. It may be desirable to optionally use a protecting group during all or portions of the above described or alternative synthetic procedures. Such protecting groups and methods for their introduction and removal are well known in the art. See Greene, T. W.; Wutz, P. G. M. "Protecting Groups In Organic Synthesis," 2$^{nd}$ ed., 1991, New York, John Wiley & Sons, Inc.

Where compounds are sufficiently basic or acidic to form stable nontoxic acid or base salts, use of the compounds as salts may be appropriate. Examples of acceptable salts are organic acid addition salts formed with acids that form an anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, hydrobromide, sulfate, nitrate, bicarbonate, and carbonate salts. Salts may be obtained using standard procedures well known in the art, for example, by reacting a sufficiently basic compound such as an amine with a suitable acid affording an acceptable anion. Alkali metals, for example, sodium, potassium or lithium, or alkaline earth metal salts, for example, calcium, of carboxylic acids can also be made.

In embodiments, the present disclosure provides a separation method, comprising chromatographing a mixture of compounds on a fused silica capillary column deactivated with a compound the formula (I) as disclosed and illustrated herein and optionally coated with a suitable or compatible stationary phase. "Deactivated," "deactivation," "deactivate," "deactivating," "passivate," and like terms refer to, for example, making or causing the native or untreated surface of the capillary column, or like article, to be less active, less interactive, or ideally inert with respect to analytes. A standard measure for the quality of inertness or relative deactivation of a chromatographic system is to measure the response of the system to sequentially lower levels of an active or difficult to measure compound. Assuming the detector has a linear response across the range of quantities of compounds to be measured, this calibration curve should be essentially flat. The flame ionization detector (FID) is considered to have a linear response for virtually all compounds within the detection limits of the detector. 2,4-Dinitrophenol (2,4-DNP) is generally regarded as one of the more difficult compounds to detect quantitatively at low levels by GC. By using on-column injection, the contribution of active sites in the injector can be eliminated. Therefore, a comparison of response for 2,4-dinitrophenol relative to a benign hydrocarbon using different capillary columns utilizing on-column injection and FID detection across a range of analyte concentrations will yield calibration curves that can be used to quantify the relative inertness of each capillary column.

Using the above technique, a series of samples with successively increasing amounts of 2,4-dinitrophenol and 1,4- dichlorobenzene as the benign internal standard was analyzed on a column deactivated with, for example, a hybrid polymethylhydrosiloxane of the disclosure and compared to the same series analyzed on a standard commercially available DB-5ms column. The relative responses measured at each concentration are recorded in Table 1.

TABLE 1

Relative response factor (RRF) for 2,4-dinitrophenol relative to 1,4-dichlorobenzene.

| 2,4-DNP ng on-column | Hybrid Column RRF | DB-5 ms Column RRF |
| --- | --- | --- |
| 100 | 0.52 | 0.54 |
| 50 | 0.53 | 0.55 |
| 25 | 0.53 | 0.48 |
| 10 | 0.50 | 0.45 |
| 5 | 0.48 | 0.40 |
| 2.5 | 0.42 | 0.36 |
| 1 | 0.38 | 0.31 |

RRF = (analyte peak area/ng)/(reference peak area/ng). On-column injection, FID detection. Column dimensions: 30 meter × 0.250 mm i.d. × 0.25 micron film DB-5 ms stationary phase.

A plot of the data (RRF v. ng of 2,4-dinitrophenol on the column) provides respective calibration curves and response linearities of the two columns which shows that the hybrid column deactivation has a greater RRF compared to a DB-5ms column in the range of about 0 to about 40 ng.

Generally acceptable linearity is considered to be less than about a 10% reduction in relative response. An excellent column would maintain this level of linearity to at least 10 ng of 2,4-DNP on-column. As can be seen in the plotted data, the DB-5ms column is hovering around 10% reduction in RRF at the 25 ng level while the hybrid deactivated column does not drop below 10% loss in response until somewhere below the 5 ng on-column level.

The disclosure also provides a separation method, including chromatographing a mixture of compounds with the article of the disclosure in a chromatograph. "Chromatographing," "chromatography," or like terms refer to, for example, the process of separating analytes, such as organic compounds, from one another, such as where a sample mixture is vaporized and injected into a stream of carrier gas (as nitrogen, hydrogen or helium) moving through a column containing a stationary phase composed of a liquid or particulate solid and is separated into its component compounds according to their affinity for the stationary phase. Chromatographic procedures are known and can include one or more of the following steps, for example, dissolving a sample in a solvent, contacting the resulting sample solution in liquid or vapor form such as by liquid injection within the column, separating the compounds in the sample by eluting with a suitable carrier gas, detecting or collecting the separated compounds, and displaying the order of elution and quantity of compounds eluted. In embodiments, the compounds, articles, and methods of the present disclosure may be applicable to other separation applications in addition to capillary gas chromatography.

The separation and deactivation methods, in embodiments, are preferably accomplished with a compound of the formula (I) having the formula (II)

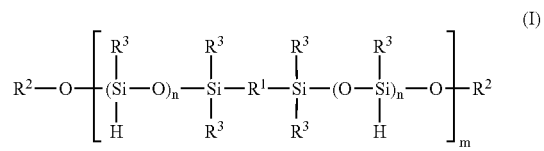

wherein
$R^1$ is
1,4-substituted $-(CH_2)_k-Ar-(CH_2)_k-$, or
1,4-substituted $(C_1-C_4)$alkyl substituted $-(CH_2)_k-Ar-(CH_2)_k-$;
$R^2$ is $-Si(CH_3)_3$;
$R^3$ is $-CH_3$;
k is an integer from 1 to about 5; and
n is an integer from 1 to about 4, and the coated stationary phase is, for example, a 5% diphenyl-95% dimethylpolysiloxane, or like dialkylpolysiloxanes.

The separation methods provide, in embodiments, superior and unexpected chromatographic separation results, for example, wherein tailing of individual peaks in the chromatogram are reduced, such as by from about 10 to 95 percent, or wherein tailing of individual peaks in the chromatogram are entirely eliminated. There is also observed a reduction in the irreversible adsorption of active compounds on the column that can lead to non-linear detection of the compounds at low levels, such as less than about ten nanograms (<10 ng). Irreversible adsorption and non-linear detection can occur with, for example, acidic compounds, such as pentachlorophenol, 2,4-dinitrophenol, and like compounds, or basic compounds such as primary amines, and like compounds. "Tailing," "tailed," "tail," and like terms refer to reversible adsorption of analytes on active sites resulting in increased retention of a portion of the sample. Partial increased retention of a portion of the sample can cause skewing of the sample peak on the trailing edge or tail of the chromatogram trace.

In embodiments, the separation method can be accomplished at low or ambient temperatures, for example, from about 0 to about 40° C., at elevated temperatures from about 40 to about 450° C., or sequentially both. In embodiments, the separation method of the disclosure can also be accomplished at subambient temperatures, for example, from about −50 to about 0° C., for example, for highly volatile samples.

The method also provides, in embodiments, superior chromatographic results, for example, wherein the resolution of individual peaks in the chromatogram are enhanced. "Resolution," "resolved," and like terms refer generally to the ability to physically and electronically detect, measure, or distinguish a signal which is specific to a single compound with respect to background noise, neighboring compound peaks in the chromatogram, or other distortions or interference on the single compound signal.

Resolution of two compounds in gas chromatography is generally influenced by two main factors: the relative retention of the two compounds, and the peak width of the detector response. This relationship is evident in the equation for resolution (Rs):

$$Rs=1.177[(T_{R(2)}-T_{R(1)}/W_{h(1)}+W_{h(2)}],$$

where $TR_{(1)}$=retention time of the first peak, $T_{R(2)}$=retention time of the second peak, $W_{h(1)}$=peak width at half height of the first peak and $W_{h(2)}$=peak width at half height of the second peak (see *High Resolution Gas Chromatography, 2$^{nd}$* ed., R. R. Freeman, editor, Hewlett-Packard Company, 1981). From the above equation it is evident that when comparing two columns of the same dimensions coated with the same phase ratio of the same stationary phase, the only factor influencing resolution is the peak width at half height. Loss of resolution due to tailing is generally only a problem with closely eluting peaks and is difficult, but not impossible, to demonstrate. In this situation the height of the valley between the peaks is measured as a percentage of the height of the shorter peak in the pair. Although active sites on the column surface or in the stationary phase can distort the peak and increase width for more polar and active analytes, for most compounds peak width is a direct measurement of the quality and uniformity of the stationary phase coating. This then becomes a direct measurement of the compatibility of the underlying surface deactivation or pre-treatment with the overlying stationary phase polymer.

Ignoring the contribution of the injector and detector, the chromatographic efficiency of the capillary column will determine the peak width of the detected analyte bands as they elute from the column through the detector. The more uniform the stationary phase coating is in a capillary column, the higher it's efficiency. The wetability of the deactivated surface determines the quality of the stationary phase coating. The effectiveness of the deactivating surface treatment can be quantified by measuring the chromatographic efficiency generated by the capillary column in terms of height equivalent to a theoretical plate ($h_{meas}$) relative to the calculated maximum possible efficiency a column of like dimensions could theoretically generate, or the minimum height equivalent to a theoretical plate ($h_{min}$). The theoretical achievable efficiency has been described (see Golay, M. J. E., in *Gas Chromatography* 1958, D. H. Desty, ed., Butterworth, London, 1958) as:

$$h_{min} = r_o[(1+6k+11k^2)/3(1+k)^2]_{1/2}$$

where $r_o$=radius of the capillary column and $k=(T_R-T_M)/T_M$, where $T_R$=retention time of peak and $T_M$=retention time of methane or an unretained peak (see *Gas Chromatography with Glass Capillary Columns*, $2^{nd}$ ed., by W. Jennings, Academic Press, New York, 1980). The measured height equivalent to a theoretical plate is given by the following equation:

$$h_{meas} = L/n$$

where L is the column length and n is the total number of theoretical plates (3) as defined as:

$$n = 5.54(T_R/W_h)^2$$

Figure 2:
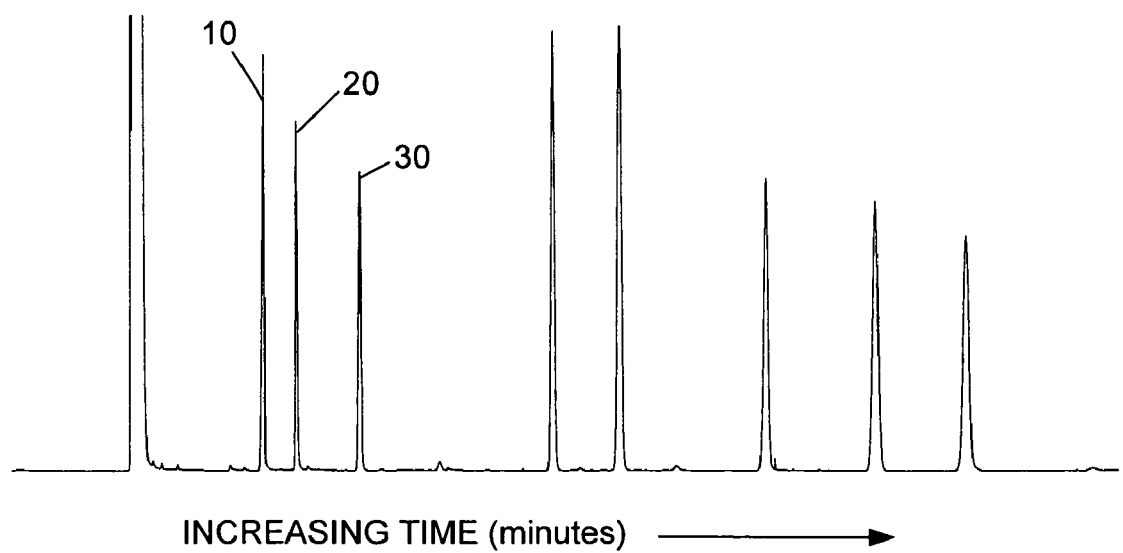
FIG. 2 illustrates a chromatogram of the same mixture of compounds of FIG. 1 separated on a capillary column deactivated with a polyhydrosiloxane compound, in embodiments of the present disclosure.

Additionally or alternatively, the efficiency of the hybrid polymethylhydrosiloxane deactivated capillary column can be quantified by measuring the coating efficiency generated by peak seven (tetradecane) in FIG. 2. This peak delivers a coating efficiency (CE) of 93%, which is generated by the following equation:

$$CE = (h_{min}/h_{meas}) \; 100\%.$$

In embodiments, the present disclosure provides a method of deactivating a fused silica capillary column, or like surfaces having reactive or active hydroxyl groups, such as Ti—OH, Al—OH, Fe—OH, or like active hydroxyl groups, comprising: treating the column with a compound of the abovementioned formula (I). One preferred compound of formula (I) is of the formula wherein $R^1$ is 1,4-substituted —$CH_2$—$C_6H_4$—$CH_2$—, 1,4-substituted —$CH_2$—$CH_2$—$C_6H_4$—$CH_2$—$CH_2$—, or combinations thereof; ($C_1$-$C_4$)alkyl substituted 1,4-substituted —$CH_2$—$C_6H_4$—$CH_2$—, ($C_1$-$C_4$) alkyl substituted 1,4-substituted —$CH_2$—$CH_2$—$C_6H_4$— $CH_2$—$CH_2$—, or combinations thereof, or Ar—CH=, or ($C_1$-$C_4$)alkyl substituted Ar—CH=, or combinations thereof; $R^2$ is —$Si(CH_3)_3$; $R_3$ is —$CH_3$; n is an integer from 1 to about 5; and m is an integer from 1 to about 5. Another preferred compound of formula (I) is the abovementioned formula (II).

In embodiments, treating comprises, contacting the fused silica capillary with, for example, a solution of the compound of the formula (I); and heating the contacted column at from about 280 to about 350° C., from about 1 to about 20 hours. The method of treating can further comprise coating the treated column with a stationary phase. "Treat," "treatment," "treating," and the like terms refer to, in the context of preparing the article of the disclosure, at least contacting a capillary column or like article with a compound, oligomer, copolymer, or mixtures thereof, of the disclosure, and optionally heating the contacted column for a time and at a temperature to effect an association between the surface of the column and the compound. The association is preferably and predominantly a chemical reaction resulting in chemical bond formation between the contacted surface of the column and the compound. The association can also include a close proximate relation between the contacted surface of the column and the compound resembling, for example, a non-covalently bonded surface coating.

For a general discussion of capillary column deactivation fundamentals, practices, and examples, see for example, T. Welsch, et al., *HRC&CC*, 11 (1988) 471; T. Welsch, et al., *Chromatographia*, 10 (1977) 22; L. Blomberg, et al., *Proceedings of the Fourth International Symposium on Capillary Chromatography*, Huethig, Heidelberg (1981) pp 73-89; C. L. Woolley, et al., *HRC&CC*, 7 (1984) 329; K. E. Markides, et al., *HRC&CC*, 8 (1985) 741; and Grob, K., "Making and Manipulating Capillary Columns for Gas Chromatography," Huethig, Heidelberg, 1986, the entireties of which are incorporated by reference herein.

In embodiments, the present disclosure provides an article comprising: a fused silica capillary column treated with the aforementioned compound of the formula (I), and coated with a stationary phase. A preferred compound of the formula (I) is the abovementioned compound of formula (II), and one possible stationary phase is, for example, 5% diphenyl-95% dimethylpolysiloxane.

In gas chromatography a source of undesirable interaction of analytes with the capillary wall is, for example, silanol groups (Si—OH) situated on the surface of inner wall of the fused silica tubing. Deactivation methods seek to eliminate or selectively modify the analyte interaction with the surface silanols. This can be accomplished, for example, by reacting the silanol groups, or like surface groups, with a chemical reagent that provides a chemically inert blocking group, such as a trimethylsilyl group (—Si—$(CH_3)_3$) to cap the silanol groups, or by sterically blocking the interaction by applying a polymeric coating over the silanol groups. Many deactivation schemes rely on a combination of both of these approaches. The known persilylation reaction with disilazanes attempts to chemically cap or block the silanols, see for example, the above mentioned T. Welsch, et al., *HRC&CC*, 11 (1988) 471. In the known disilazane deactivation there is evidence that there is some polymerization of the disilazane materials used for deactivation. While not desired to be limited by theory, this polymerization is believed to lead to some silanol group masking and steric hindrance to silanol surface interaction. However, this is believed to be a minor mode or mechanism of action of the present disclosure. In embodiments, the interaction of the polyhydrosiloxane compounds of the present disclosure and surface silanol groups can be a combination of both silanol capping reaction and polymeric barrier coating.

In general, the known disilazane deactivation reaction tends to create a basic surface due to the presence of NH groups on unreacted silazane, whereas in one aspect, the polyhydrosiloxane deactivation reaction of the present disclosure produces an acidic surface due to the acidic nature of unreacted SiH. An "acidic surface" refers to a column surface having acidic properties within the Lewis, Bronstedt, or both concepts (i.e., electron pair acceptor or a proton donor). However, both the disilazane and the hydrosiloxane routes tend to approach a neutral surface when the respective reactions with silanols are driven toward completion.

In one aspect, the disclosure provides backbone-integrated or hybrid polyalkylhydrosiloxanes. One advantage of these compounds over the corresponding pendant polyalkylhydrosiloxanes (which pendant siloxanes are appended to the polymer backbone or chain) follows. Bulky aromatic or heteroaromatic pendant groups, such as a pendant aryl or phenyl containing polyhydrosiloxanes, can often lead to a porous surface layer that can cause distortion, such as skewing, of hydrocarbon analyte peaks due to what appears to resemble adsorption chromatography (see FIG. 5 and Comparative Example 7). Although not desired to be limited by theory, the mechanism may involve disruption of the interaction of the polyhydrosiloxane with the fused silica surface, thereby leaving portions of the polymer chain free for intra- and interchain cross-linking, if some of the silylhydride groups are first hydrolyzed. This could potentially lead to the formation of a porous organosilica structure that could cause the type of adsorption behavior observed. Although the insertion of the aromatic or heteroaromatic groups into the polymer chain backbone can also interrupt the binding of the hydrosiloxane to the fused silica surface, these bridges or spacers having aromatic- or pi-electron type character tend to increase chain rigidity, thereby countering any tendency to form intra-chain binding by reducing the possibility of the chain folding back on itself. With the backbone integrated polyalkylhydrosiloxane compounds of the present disclosure and deactivated column articles prepared therewith, the abovementioned adsorption phenomena and its concomitant chromatographic peak skewing has not been observed.

The hydrocarbon bridge or spacer in the polyalkylhydrosiloxane compounds or polymer structures can be any suitable functional group. However, one purpose of the hydrocarbon bridge or spacer and the overall hybrid polymer structure is to increase the polarity of the resulting deactivated capillary surface so as to increase its wetability by moderately polar to polar polysiloxane stationary phases. Preferred hydrocarbon bridge or spacer structures can be, for example, aromatic groups such as phenyl, tolyl, biphenyl, diphenylether, and like groups, and as illustrated herein. However, many other functional groups may be selected, as alternatives or in addition to the hydrocarbon bridge, depending on the particular requirements of a separation or sample mixture. A preferred hydrocarbon bridge or spacer functional group for the purpose of achieving good wetability of a 5% diphenyl-95% dimethylpolysiloxane stationary support, or similar polymeric stationary support is, for example, a disubstituted 1,4-xylene or para-xylene. A corresponding preferred bridging monomer for introducing para-xylene as the hydrocarbon bridge is, for example, the abovementioned α,α'-bis(dimethylmethoxysilyl)p-xylene.

In embodiments, the inclusion of one or more methylene (—CH$_2$—) or methylenyl group between the aromatic ring and the silicon atom can greatly enhance the miscibility and reactivity of the bridging monomer with a siloxane backbone forming compound, such as tetramethylcyclotetrasiloxane of the formula

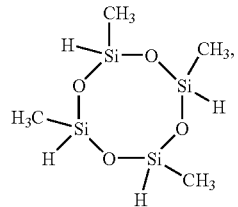

which can be used as a source of methylsilylhydride groups (Si(—CH$_3$)—H). When a 1,4-disubstituted —C$_6$H$_4$— bridge (i.e., without any alkylenyl —(CH$_2$)$_k$-substituents) was used in making the deactivating polyhydrosiloxane polymer, phase separation was observed among the resulting polymer, monomers, and oligomers, suggesting less than optimal incorporation of the divalent phenyl (—C$_6$H$_4$—) bridge into the resulting polymer.

In embodiments of the present disclosure, the compounds, methods of making, and articles produced, such as chromatography column articles, are useful in many applications, such as environmental analysis for trace toxic compounds such as chemical pollutants, pesticides and herbicides, in medical diagnostics, as a research tool for separating and analyzing complex mixtures, in therapeutic drug evaluation, in compound isolation and identification, drug production, dosage formulation and delivery, and like applications. The compounds, oligomers, or copolymers of the present disclosure can be useful in other applications, for example, organosilicone coatings, conversion coatings, coupling agents (e.g., see Pludemann, *Silane Coupling Agents*, (1982)), surface modifiers, silicone elastomer or rubber applications, such as articles or devices, and like applications.

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

EXAMPLE 1

Polyhydrosiloxane Compound Preparation. To a solvent mixture consisting of 15 mL of methylene chloride and 15 mL of acetonitrile was added 2.00 mL (1.98 g) of tetramethylcyclotetrasiloxane (79 mole % methylsilylhydride), 1.769 g α,α'-bis(dimethylmethoxysilyl)p-xylene (15 mole %), 0.532 mL (0.407 g) hexamethyldisiloxane (6 mole %), and 0.200 g Amberlyst® 15, a resin bound sulfonic acid catalyst (commercially available from Rohm and Haas Co.). This mixture was stirred for approximately 5 hours at room temperature. Then the solution was filtered to remove the catalyst resin. The solvents were removed using a rotary evaporator and the resulting polymer was used without further purification.

EXAMPLE 2

Column Deactivation. Fused silica capillary tubing was deactivated using a 1 to 2% solution of a polyhydrosiloxane of the disclosure, such as the product of Example 1, in an inert organic solvent such as pentane, hexane or toluene. A plug of this solution equal to approximately 20 to 30% of the column volume was introduced into the capillary and then pushed through at a constant rate with an inert, oxygen-free gas, such as nitrogen or argon, leaving behind a film of the hybrid polyhydrosiloxane. The ends of the capillary were flame sealed and the column was heated to about 300 to about 320° C. for about 2 to about 16 hours. Residual polymer was then rinsed out of the column with suitable organic solvents, typically such as, methanol and methylene chloride. The capillary tubing was then ready for coating with the final stationary phase polymer and as described in the literature. One preferred stationary phase is, for example, 5% diphenyl-95% dimethylpolysiloxane. For guidance on treating or coating capillary columns, see for example the abovementioned Grob reference. Other suitable stationary polymers include, for example, 100% polydimethylsiloxane, 6 to 15% cyanopropylphenyl substituted polydimethylsiloxanes, 1 to about 35% diphenyl or phenylmethyl substituted polydimethylsiloxanes, and like siloxane polymers in a similar polarity range, or combinations thereof. In embodiments, the deactivated capillary is preferably pre-cured by heating to remove the final traces of un-bound polyhydrosiloxane before the final coating with the stationary phase polymer. Thus, for example, after thoroughly rinsing and drying the deactivated column it is connected to an oxygen-free inert gas source, such as hydrogen, helium, or nitrogen, and heated to about 325° C. for from about 4 to about 24 hours while maintaining a constant gas purge.

Referring to the Figures, FIGS. 1 to 5 are chromatograms which provide a showing of comparative results for standard or traditional deactivated columns and exemplary results that can be achieved by deactivated columns using the hybrid polyalkylhydrosiloxanes of the present disclosure. The conditions, analytes, and the results for each chromatogram are discussed below.

Comparative Example 3

FIG. 1 shows a comparative chromatogram of a first mixture of analyte compounds separated on a capillary column, which had been deactivated with a known or conventional disilazane compound, see for example the abovementioned Grob reference. The test mixture of eight analyte compounds, by order of elution, included:
1) 2-ethylhexanoic acid,
2) 1,6-hexanediol,
3) 4-chlorophenol,
4) tridecane,
5) 1-methylnaphthalene,
6) 1-undecanol,
7) tetra-decane, and
8) dicyclohexylamine.

This chromatogram illustrates a typical shortcoming of certain commercially available disilazane deactivated columns, for example, where the deactivation is accomplished with a mixture of disilazanes for high temperature "persilylation" as described by Welsch and further developed by Grob, see the above mentioned references. Note the objectionable tailing (i.e., skewing of peak at or near the baseline of right shoulder) of sample peaks number 1 (10), 2 (20), and 3 (30).

EXAMPLE 4

FIG. 2 shows a chromatogram of the same mixture of analyte compounds of FIG. 1 separated on a capillary column deactivated with a polyhydrosiloxane compound, such as the product of Example 1, in embodiments of the present disclosure. Conspicuously absent was any sign of tailing on any of the sample peaks in the chromatogram, most notably peaks 1 (10), 2 (20), and 3 (30).

Comparative Example 5

Figure 3:
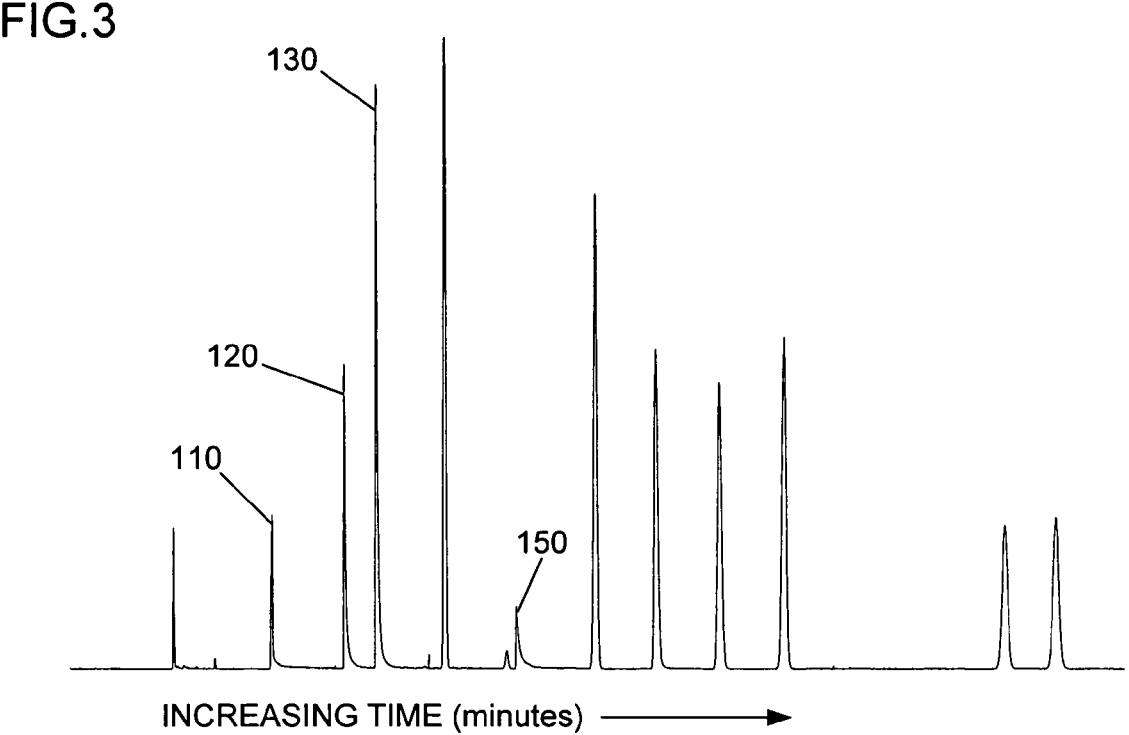
FIG. 3 illustrates another comparative chromatogram of a second mixture of analyte compounds separated on a capillary column deactivated with the known disilazane compound.

FIG. 3 shows another comparative chromatogram of a second mixture of analyte compounds separated on a capillary column deactivated with a known conventional disilazane compound chemistry, i.e., using the same column as in Comparative Example 3. In this comparative example and Example 6, a new, more stringent test mix and conditions were used (column temperature 65° C.). The second test mixture of eleven analyte compounds, by order of elution, included:
1) butyric acid,
2) 1,2-butanediol,
3) 4-picoline,
4) nonane,
5) trimethylphosphate,
6) propylbenzene,
7) 1-heptanol,
8) 3-octanone,
9) decane,
10) 1-bromoheptane, and
11) 1-nitrohexane.

This test mixture contained a more active collection of analyte components that are low molecular weight so that the test can be run at lower temperature to enhance interaction with the column surface and aggravating or limiting any potential adsorption. The tailing of sample peaks 1 (110), 2 (120), 3 (130), and 5 (150) is notable and objectionable.

EXAMPLE 6

Figure 4:
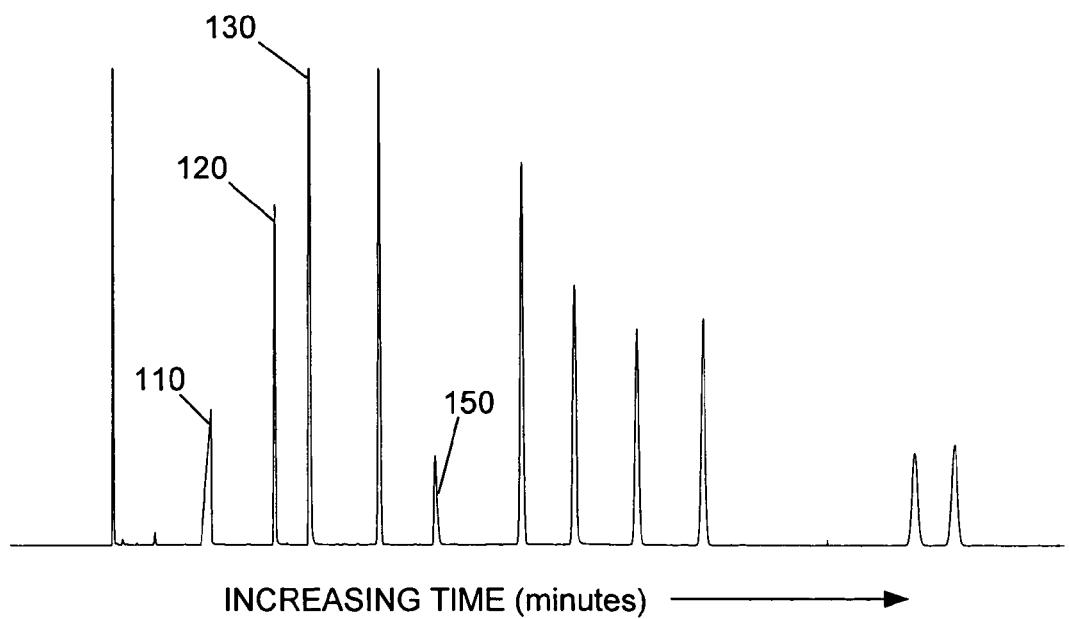
FIG. 4 illustrates a chromatogram of the same mixture of compounds of FIG. 3 separated on a capillary column deactivated with a polyhydrosiloxane compound, in embodiments of the present disclosure.

FIG. 4 shows a chromatogram of the same test mixture of compounds of FIG. 3 that were separated on a capillary column which had been deactivated with the polyhydrosiloxane compound of Examples 1 and 2 having a backbone spacer hydrocarbon moiety of the present disclosure. The absence of any tailing of the abovementioned peaks 1 (110), 2 (120), 3 (130), and 5 (150) from Comparative Example 5 is particularly noteworthy and desirable.

Comparative Example 7

Figure 5:
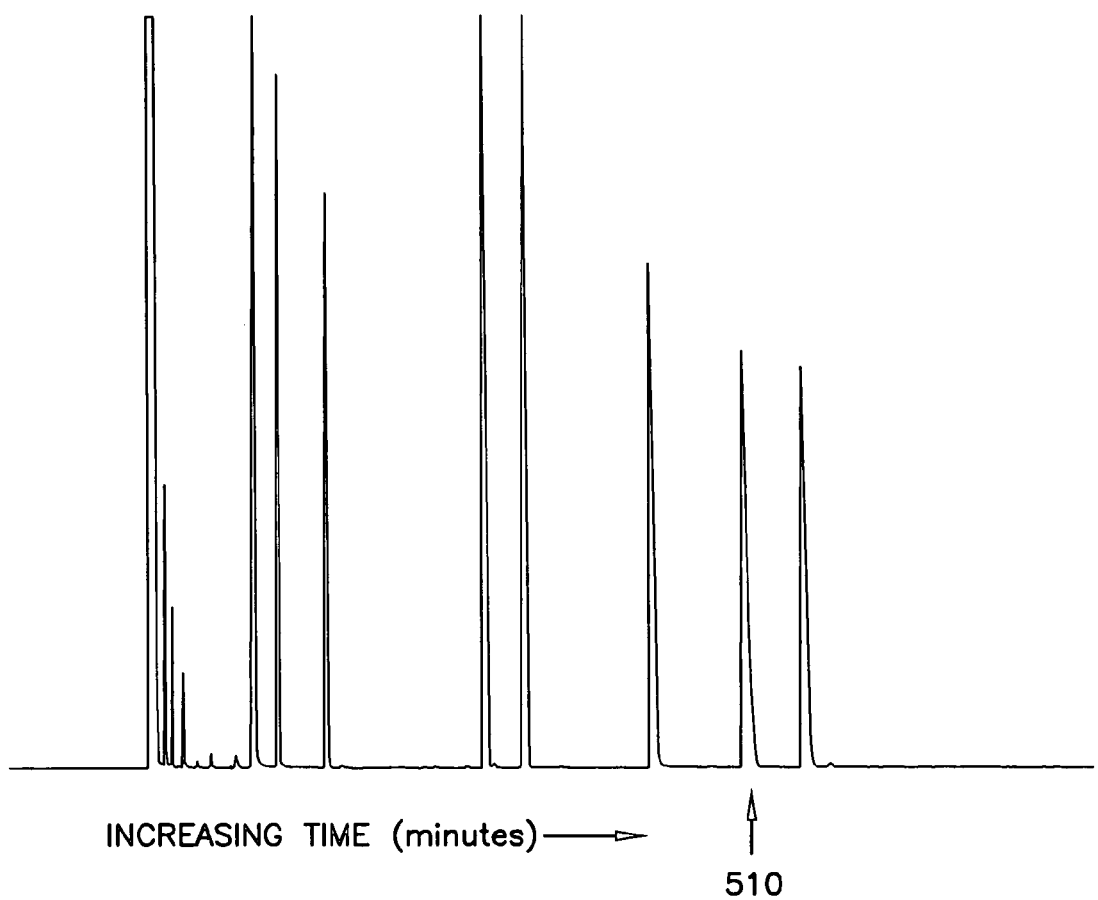
FIG. 5 illustrates a chromatogram of the same mixture of compounds of FIG. 3 separated on a capillary column deactivated with a comparative polyhydrosiloxane compound having polar pendant group(s).

FIG. 5 shows a chromatogram of the same test mixture of compounds used in Comparative Example 5 and FIG. 3 that were separated on a capillary column that had been deactivated with a phenylmethyl-polymethylhydrosiloxane copolymer compound (i.e., without a $R^1$ hydrocarbon spacer or bridge of the present disclosure) of the formula:

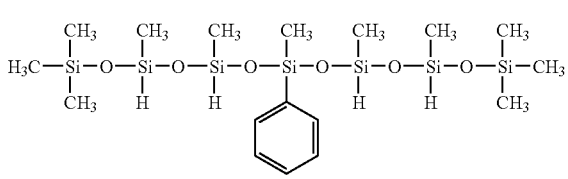

having polar pendant groups of the formula —O—Si(Ph)(Me)—O—, and prepared by conventional methods. The apparent skewing of the second-to-the-last peak (510), tetradecane, is notable. This indicates adsorption of a type typically observed on porous silica layers. This type of skewing typically can also be associated with overload or saturation of column adsorption sites.

The entire disclosure for publications, patents, and patent documents are incorporated herein by reference in their entirety, as though individually incorporated by reference. The disclosure has been described with reference to various specific embodiments and techniques. However, it should be understood that many variations and modifications are possible while remaining within the spirit and scope of the disclosure.

What is claimed is:

1. A separation method, comprising:
chromatographing a mixture of compounds on a fused silica capillary column deactivated with a compound the formula (I):

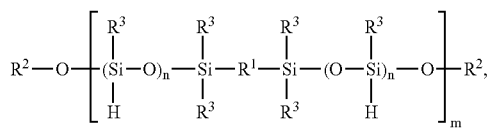

where
$R^1$ is a divalent spacer group selected from
—Ar—,
$(C_1-C_4)$alkyl substituted —Ar—,
—$(CH_2)_k$—Ar—$(CH_2)_k$—,
$(C_1-C_4)$alkyl substituted —$(CH_2)_k$—Ar—$(CH_2)_k$—,
—Ar—Ar—,
$(C_1-C_4)$alkyl substituted —Ar—Ar—,
—$(CH_2)_k$—Ar—Ar—$(CH_2)_k$—,
$(C_1-C_4)$alkyl substituted —$(CH_2)_k$—Ar—Ar—$(CH_2)_k$—,
—$(CH_2)_k$—Ar—$(CH_2)_k$—Ar—$(CH_2)_k$—,
$(C_1-C_4)$alkyl substituted —$(CH_2)_k$—Ar—$(CH_2)_k$—Ar—$(CH_2)_k$—,
—Ar—O—Ar—, $(C_1-C_4)$alkyl substituted —Ar—O—Ar—,
—$(CH_2)_k$—Ar—O—Ar—$(CH_2)_k$—,
$(C_1-C_4)$alkyl substituted —$(CH_2)_k$—Ar—O—Ar—$(CH_2)_k$—,
saturated or unsaturated —$(C_1-C_6)$alkylene-,
$(C_1-C_4)$alkyl substituted saturated or unsaturated —$(C_1-C_6)$alkylene-;
Het, $(C_1-C_4)$alkyl substituted -Het-,
—$(CH_2)_k$-Het-$(CH_2)_k$—,
$(C_1-C_4)$alkyl substituted —$(CH_2)_k$-Het-$(CH_2)_k$—,
Ar'—CH=, or
$(C_1-C_4)$alkyl substituted Ar'—CH=,
$R^2$ is an end cap group;
$R^3$ are each independently a branched or unbranched $(C_1-C_4)$alkyl or -Ph;
k is an integer from 1 to about 10;
n is an integer from 1 to about 10; and
m is an integer from 1 to about 10;
and coated with a stationary phase.

2. The method of claim 1 wherein tailing of individual peaks in the chromatogram are reduced by from about 10 to about 95 percent.

3. The method of claim 1 wherein tailing of individual peaks in the chromatogram are eliminated.

4. The method of claim 1 wherein resolution of individual peaks in the chromatogram are enhanced.

5. The method of claim 1 wherein the compound the formula (I) is of the formula (II)

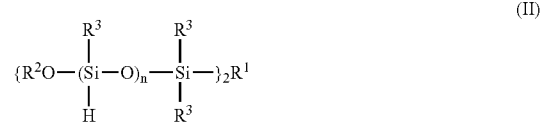

wherein
$R^1$ is
—Ar—$(CH_2)_k$—,
$(C_1-C_4)$alkyl substituted —Ar—$(CH_2)_k$—,
1,4-substituted —$(CH_2)_k$—Ar—$(CH_2)_k$—, or
1,4-substituted $(C_1-C_4)$alkyl substituted —$(CH_2)_k$—Ar—$(CH_2)_k$—;
$R^2$ is —Si$(CH_3)_3$;
$R^3$ is —$CH_3$;
k is an integer from 1 to about 5; and
n is an integer from 1 to about 4, and
the coated stationary phase is polysiloxane containing polymer.

6. The method of claim 1 wherein separation is accomplished at from about −50 to about 40° C.

7. The method of claim 1 wherein separation is accomplished at from about 40 to about 450° C.

8. A method of deactivating a fused silica capillary column, comprising:
treating the column with a compound of the formula (I)

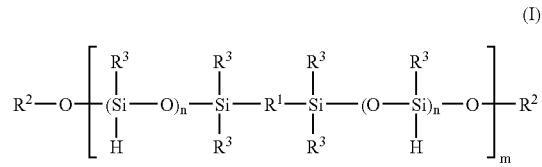

where
$R^1$ is a divalent spacer group selected from
—Ar—,
$(C_1-C_4)$alkyl substituted —Ar—,
—$(CH_2)_k$—Ar—$(CH_2)_k$—,
$(C_1-C_4)$alkyl substituted —$(CH_2)_k$—Ar—$(CH_2)_k$—,
—Ar—Ar—,
$(C_1-C_4)$alkyl substituted —Ar—Ar—,
—$(CH_2)_k$—Ar—Ar—$(CH_2)_k$—,
$(C_1-C_4)$alkyl substituted —$(CH_2)_k$—Ar—Ar—$(CH_2)_k$—,
—$(CH_2)_k$—Ar—$(CH_2)_k$—Ar—$(CH_2)_k$—,
$(C_1-C_4)$alkyl substituted —$(CH_2)_k$—Ar—$(CH_2)_k$—Ar—$(CH_2)_k$—,
—Ar—O—Ar—, $(C_1-C_4)$alkyl substituted —Ar—O—Ar—,
—$(CH_2)_k$—Ar—O—Ar—$(CH_2)_k$—,
$(C_1-C_4)$alkyl substituted —$(CH_2)_k$—Ar—O—Ar—$(CH_2)_k$—,
saturated or unsaturated —$(C_1-C_6)$alkylene-,
$(C_1-C_4)$alkyl substituted saturated or unsaturated —$(C_1-C_6)$alkylene-;
Het, $(C_1-C_4)$alkyl substituted -Het-,
—$(CH_2)_k$-Het-$(CH_2)_k$—,
$(C_1-C_4)$alkyl substituted —$(CH_2)_k$-Het-$(CH_2)_k$—,
Ar'—CH=, or
$(C_1-C_4)$alkyl substituted Ar'—CH=;
$R^2$ is an end cap group;
$R^3$ are each independently a branched or unbranched $(C_1-C_4)$alkyl or —Ph;
k is an integer from 1 to about 10;
n is an integer from 1 to about 10; and m is an integer from 1 to about 10.

9. The method of claim 8 wherein
R$^1$ is
—(CH$_2$)$_k$—Ar—(CH$_2$)$_k$—,
(C$_1$-C$_4$)alkyl substituted —(CH$_2$)$_k$—Ar—(CH$_2$)$_k$—,
Het,
(C$_1$-C$_4$)alkyl substituted -Het-,
—CH$_2$-Het-CH$_2$—,
(C$_1$-C$_4$)alkyl substituted —CH$_2$-Het-CH$_2$—,
—Ar—(CH$_2$)$_k$—, or
(C$_1$-C$_4$)alkyl substituted —Ar—(CH$_2$)$_k$—;
R$^2$ is —Si(CH$_3$)$_3$;
R$^3$ is —CH$_3$;
k is an integer from 1 to about 5;
n is an integer from 1 to about 5; and
m is an integer from 1 to about 5.

10. The method of claim 8 wherein the compound of formula (I) is of the formula (II)

$$\{R^2O-(Si(R^3)(H)-O)_n-Si(R^3)(R^3)-\}_2 R^1 \qquad (II)$$

wherein
R$^1$ is of the formula

[structures showing para-substituted benzene with CH$_2$ linkers, meta-substituted benzene with propylene linkers, and para-substituted benzene with CH$_2$ and propylene linkers]

or combinations thereof;
R$^2$ is —Si(CH$_3$)$_3$;
R$^3$ is —CH$_3$; and
n is 4.

11. The method of claim 8 wherein treating comprises:
contacting the fused silica capillary column with the compound of the formula (I); and
heating the contacted column at from about 280 to about 350° C., for from about 1 to about 20 hours.

12. The method of claim 10 further comprising coating the treated column with a material forming a stationary phase.

13. The method of claim 12 wherein the stationary phase material is selected from the group consisting of polydimethylsiloxane, a diphenyl substituted dimethylpolysiloxane, a cyanopropylphenyl substituted polydimethylsiloxane, a diphenyl substituted polydimethylsiloxane, a phenylmethyl substituted polydimethylsiloxane, and combinations thereof.

14. An article comprising:
a fused silica capillary column treated with a compound of the formula (I)

$$R^2-O-[(Si(R^3)(H)-O)_n-Si(R^3)(R^3)-R^1-Si(R^3)(R^3)-(O-Si(R^3)(H))_n-O]_m-R^2 \qquad (I)$$

where
R$^1$ is a divalent spacer group selected from
—Ar—,
(C$_1$-C$_4$)alkyl substituted —Ar—,
—(CH$_2$)$_k$—Ar—(CH$_2$)$_k$—,
(C$_1$-C$_4$)alkyl substituted —(CH$_2$)$_k$—Ar—(CH$_2$)$_k$—,
—Ar—Ar—,
(C$_1$-C$_4$)alkyl substituted —Ar—Ar—,
—(CH$_2$)$_k$—Ar—Ar—(CH$_2$)$_k$—,
(C$_1$-C$_4$)alkyl substituted —(CH$_2$)$_k$—Ar—Ar—(CH$_2$)$_k$—,
—(CH$_2$)$_k$—Ar—(CH$_2$)$_k$—Ar—(CH$_2$)$_k$—,
(C$_1$-C$_4$)alkyl substituted —(CH$_2$)$_k$—Ar—(CH$_2$)$_k$—Ar—(CH$_2$)$_k$—,
—Ar—O—Ar—, (C$_1$-C$_4$)alkyl substituted —Ar—O—Ar—,
—(CH$_2$)$_k$—Ar—O—Ar—(CH$_2$)$_k$—,
(C$_1$-C$_4$)alkyl substituted —(CH$_2$)$_k$—Ar—O—Ar—(CH$_2$)$_k$—,
saturated or unsaturated —(C$_1$-C$_6$)alkylene-,
(C$_1$-C$_4$)alkyl substituted saturated or unsaturated —(C$_1$-C$_6$)alkylene-;
Het, (C$_1$-C$_4$)alkyl substituted -Het-,
—(CH$_2$)$_k$-Het-(CH$_2$)$_k$—,
(C$_1$-C$_4$)alkyl substituted —(CH$_2$)$_k$-Het-(CH$_2$)$_k$—,
Ar'—CH=, or
(C$_1$-C$_4$)alkyl substituted Ar'—CH=;
R$^2$ is an end cap group;
R$^3$ are each independently a branched or unbranched (C$_1$-C$_4$)alkyl or -Ph;
k is an integer from 1 to about 10;
n is an integer from 1 to about 10; and
m is an integer from 1 to about 10, and
optionally coated with a material forming a stationary phase.

15. The article of claim 14 wherein the compound of the formula (I) is the formula (II)

$$\{R^2O-(Si(R^3)(H)-O)_n-Si(R^3)(R^3)-\}_2 R^1 \qquad (II)$$

wherein
R$^1$ is para-substituted —(CH$_2$)$_k$—C$_6$H$_4$—(CH$_2$)$_k$—;
R$^2$ is —Si(CH$_3$)$_3$;
R$^3$ are each —CH$_3$;
k is an integer from 1 to about 4; and
n is 4; and
the stationary phase is 5% diphenyl-95% dimethylpolysiloxane.

* * * * *

UNITED STATES PATENT AND TRADEMARK OFFICE
CERTIFICATE OF CORRECTION

PATENT NO. : 7,390,349 B2  Page 1 of 1
APPLICATION NO. : 10/913611
DATED : June 24, 2008
INVENTOR(S) : Lautamo It is certified that error appears in the above-identified patent and that said Letters Patent is hereby corrected as shown below:

In column 19, line 16, in Claim 1, after "compound" insert -- of --.

In column 19, line 60, in Claim 2, delete "are" and insert -- is --, therefor.

In column 19, line 63, in Claim 3, delete "are" and insert -- is --, therefor.

In column 19, line 65, in Claim 4, delete "are" and insert -- is --, therefor.

In column 19, line 66, in Claim 5, delete "the" and insert -- of --, therefor.

In column 20, line 19, in Claim 5, delete "I" and insert -- 1 --, therefor.

In column 20, line 59, in Claim 8, after "$(CH_2)_k-$," insert -- $-Ar-(CH_2)_k-$, --.

In column 20, line 60, in Claim 8, delete "$-(CH_2)_k-Het-(CH_2)_k-$," and insert -- $-Ar-(CH_2)_k-$, --, therefor.

In column 22, line 35, in Claim 14, after "$(CH_2)_k-$," insert -- $-Ar-(CH_2)_k-$, (C1–C4) alkyl substituted $-Ar-(CH_2)_k-$, --.

Signed and Sealed this

Eighteenth Day of November, 2008

JON W. DUDAS
*Director of the United States Patent and Trademark Office*